US00PP17797P2

(12) United States Plant Patent
Sakazaki

(10) Patent No.: US PP17,797 P2
(45) Date of Patent: Jun. 12, 2007

(54) ***PHLOX* PLANT NAMED 'USPHLOTM6'**

(50) Latin Name: *Phlox hybrida*
Varietal Denomination: USPHLOTM6

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 11/273,496

(22) Filed: Nov. 14, 2005

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Phlox* plant named 'USPHLOTM6', characterized by its upright and outwardly spreading plant habit; vigorous growth habit; attractive white-colored flowers; freely and continuous flowering habit; and good garden performance.

1 Drawing Sheet

Botanical designation: *Phlox hybrida.*
Cultivar denomination: 'USPHLOTM6'.

BACKGROUND OF THE INVENTION

The present Invention relates to a new and distinct cultivar of *Phlox* plant, botanically known as *Phlox hybrida,* and hereinafter referred to by the cultivar name USPHLOTM6.

The new *Phlox* is a product of a planned breeding program conducted by the Inventor in Hikone Shiga, Japan. The objective of the breeding program was to create new pot-type *Phlox* cultivars with numerous attractive flowers.

The new *Phlox* originated from a cross-pollination made by the Inventor on Mar. 23, 2000 in Hikone Shiga, Japan of two unidentified selections of *Phlox hybrida,* not patented. The new *Phlox* was discovered and selected by the Inventor as a flowering plant within the progeny of the stated cross-pollination in a controlled environment in Bonsall, Calif., on May 19, 2001.

Asexual reproduction of the new cultivar by terminal cuttings at Bonsall, Calif. since May 19, 2001, has shown that the unique features of this new *Phlox* are stable and reproduced true to type in successive generations.

SUMMARY OF THE INVENTION

Plants of the cultivar USPHLOTM6 have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'USPHLOTM6'. These characteristics in combination distinguish 'USPHLOTM6' as a new and distinct cultivar:

1. Upright and outwardly spreading plant habit.
2. Vigorous growth habit.
3. Attractive white-colored flowers.
4. Freely and continuous flowering habit.
5. Good garden performance.

Plants of the new *Phlox* differ from plants of the parent selections in the following characteristics:

1. Plants of the new *Phlox* are more vigorous than plants of the parent selections.
2. Plants of the new *Phlox* haver larger flowers than plants of the parent selections.
3. Plants of the new *Phlox* flower for a longer period of time than plants of the parent selections.

Plants of the new *Phlox* can be compared to plants of the *Phlox* cultivar Silvermine, disclosed in U.S. Plant Pat. No. 12,764. In side-by-side comparisons conducted in Southern California, plants of the new *Phlox* differed primarily from plants of the cultivar Silvermine as plants of the cultivar Silvermine had variegated leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Phlox.*

The photograph at the bottom of the sheet comprises a side perspective view of a typical flowering plant of 'USPHLOTM6' grown in a container.

The photograph at the top of the sheet is a close-up view of typical flowers of 'USPHLOTM6'.

DETAILED BOTANICAL DESCRIPTION

In the following description, color references are made to The Royal Horticultural Society Colour Chart, 1995 Edition, except where general terms of ordinary dictionary significance are used. Plants grown in 15-cm containers were used for the aforementioned photographs and following description. Plants were about two months from planting rooted cuttings. Plants were grown under conditions which closely approximate commercial production conditions during the summer in Bonsall, Calif. in an outdoor nursery. During the production period, day temperatures ranged from 21° C. to 35° C. and night temperatures ranged from 10° C. to 18° C.

Botanical classification: *Phlox hybrida* cultivar USPHLOTM6.

Parentage:

*Female parent.*—Unidentified selection of *Phlox hybrida,* not patented.

*Male parent.*—Unidentified selection of *Phlox hybrida,* not patented.

Propagation:

*Type cutting.*—Vegetative cuttings.

*Time to initiate roots.*—About one to two weeks.

*Time to produce a rooted young plant.*—About three to four weeks.

*Root description.*—Fine, fibrous.

*Rooting habit.*—Freely branching; moderately dense.

Plant description:

*Plant form/habit.*—Upright and outwardly spreading plant habit; broad inverted triangle; vigorous growth habit. Freely branching with about four main stems per plant each with multiple secondary lateral branches.

*Plant height.*—About 24 cm.

*Plant width* (*spread*).—About 43 cm.

*Lateral branches.*—Length: About 28 cm. Diameter: About 3.5 mm. Internode length: About 1.5 cm. Strength: Strong. Texture: Pubescent. Color: 146A.

*Foliage description.*—Arrangement: Alternate, simple; sessile. Length: Abut 2.5 cm. Width: About 8 mm. Shape: Narrowly elliptic to lanceolate. Apex: Acute to acuminate. Base: Clasping to slightly auriculate. Margin: Entire. Texture, upper and lower surfaces: Slightly rough; pubescent. Venation pattern: Pinnate; arcuate. Color: Developing leaves, upper and lower surfaces: 146A. Fully expanded leaves, upper surface: 147A. Fully expanded leaves, lower surface: 147B. Venation, upper and lower surfaces: 146C.

Flower description:

*Flower type/habit.*—Single, rounded salverform flowers arranged in terminal panicles; flowers face upright and outward. Panicles roughly hemispherical in shape. Freely flowering habit with about 46 flower buds and flowers per inflorescence.

*Fragrance.*—None detected.

*Natural flowering season.*—Continuously flowering from spring through fall in Southern California. Flowers persistent.

*Postproduction longevity.*—Flowers last about four to five days on the plant.

*Inflorescence height.*—About 3.5 cm.

*Inflorescence diameter.*—About 5 cm.

*Flower buds.*—Height: About 1.9 cm. Diameter: About 5 mm. Shape: Elongated ovoid. Color: 145D.

*Flowers.*—Diameter: About 2.7 cm. Depth: About 2.2 cm. Throat diameter, distal: About 1.5 mm. Tube diameter, proximal: About 2 mm. Tube length: About 1.5 cm.

*Petals.*—Quantity per flower: Typically five in a single whorl; petals fused at the base into a narrow tube. Lobe length: About 1.3 cm. Lobe width: About 1.2 cm. Lobe shape: Obovate. Lobe apex: Rounded; slightly serrate. Lobe margin: Entire; slightly undulate. Texture: Lobes, upper and lower surfaces: Smooth, glabrous; satiny. Throat: Smooth, glabrous. Tube: Pubescent. Color: Developing petals, upper surface: 157C. Developing petals, lower surface: 157D. Fully expanded petals, upper surface: 155A; towards the base, 157A; venation, 155A. Fully expanded petals, lower surface: 155A; venation, 157A. Throat: 157B; venation, 157A. Tube: 157A; venation, 157A.

*Sepals.*—Quantity per flower: Typically five in a single whorl, fused; narrow tubular calyx. Length: About 5 mm. Width: About 1 mm. Shape: Lanceolate; recurved. Apex: Acuminate. Margin: Entire. Texture, upper and lower surfaces: Pubescent. Color, upper and lower surfaces: 146A.

*Peduncles.*—Length: About 1.2 cm. Diameter: About 1 mm. Orientation: Erect to about 45° from vertical. Strength: Strong. Texture: Pubescent. Color: 144B.

*Pedicels.*—Length: About 7 mm. Diameter: About 1 mm. Orientation: About 45° from vertical. Strength: Strong. Texture: Pubescent. Color: 144A.

*Reproductive organs.*—Stamens: Quantity per flower: Typically five. Anther shape: Oblong. Anther size: About 1 mm by 2 mm. Anther color: 11A. Pollen amount: Scarce. Pollen color: 12A. Pistils: Quantity per flower: Typically one. Pistil length: About 5 mm. Stigma shape: Tri-parted. Stigma color: 1A. Style length: About 2 cm. Style color: 145B. Ovary color: 144A.

Disease/pest resistance: Plants of the new *Phlox* have not been noted to be resistant to pathogens and pests common to *Phlox*.

Garden performance: Plants of the new *Phlox* have been observed to have good garden performance and tolerate rain, wind and temperatures ranging from −5° C. to 38° C.

It is claimed:

1. A new and distinct cultivar of *Phlox* plant named 'USPHLOTM6', as illustrated and described.

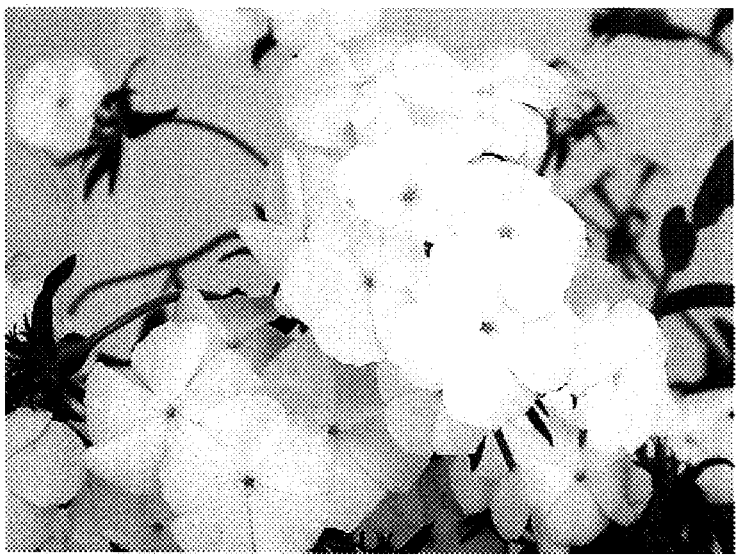
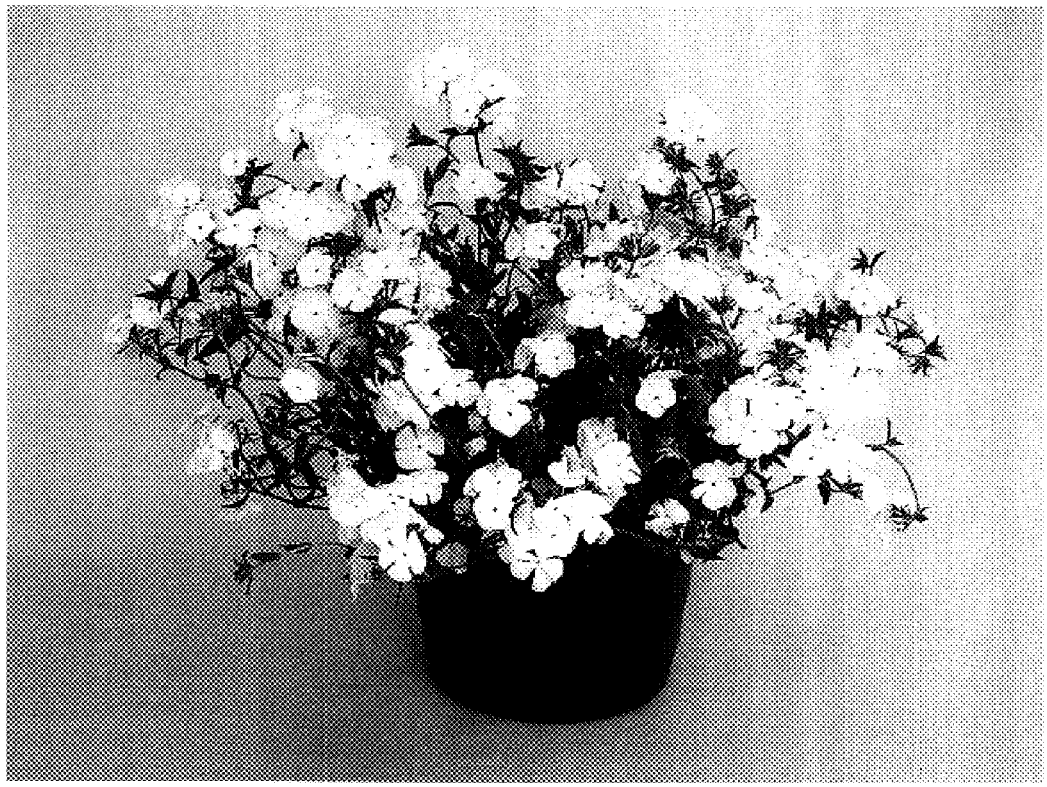

* * * * *